United States Patent [19]
Gabriel

[11] Patent Number: 5,667,067
[45] Date of Patent: Sep. 16, 1997

[54] DISPOSABLE RECEPTACLE FOR REMOVING BLADES FROM A SCALPEL

[76] Inventor: Rodney A. Gabriel, 6248 Damask Ave., Los Angeles, Calif. 90056

[21] Appl. No.: 564,179

[22] PCT Filed: Nov. 15, 1994

[86] PCT No.: PCT/US94/13168

§ 371 Date: Dec. 11, 1995

§ 102(e) Date: Dec. 11, 1995

[87] PCT Pub. No.: WO96/14774

PCT Pub. Date: May 23, 1996

[51] Int. Cl.⁶ .............................. B65D 83/10; B23P 19/04
[52] U.S. Cl. .............. 206/355; 29/239; 29/278; 206/359; 211/60.1
[58] Field of Search .................. 206/352, 354, 206/355, 359, 360; 29/239, 278; 30/337, 339; 211/60.1, 71

[56] References Cited

U.S. PATENT DOCUMENTS

| | | |
|---|---|---|
| 4,168,177 | 9/1979 | Gaskell et al. |
| 4,270,416 | 6/1981 | Thompson. |
| 4,344,532 | 8/1982 | Eldridge, Jr. |
| 4,395,807 | 8/1983 | Eldridge, Jr. |
| 4,466,539 | 8/1984 | Frauenhoffer. |
| 4,730,376 | 3/1988 | Yamada. |
| 4,903,390 | 2/1990 | Vidal et al. |
| 4,998,334 | 3/1991 | Pemberton ........................... 29/239 |
| 5,083,817 | 1/1992 | Kromer et al. |
| 5,163,553 | 11/1992 | Cantwell et al. |
| 5,301,807 | 4/1994 | Donahue. |
| 5,363,958 | 11/1994 | Horan .................................. 206/356 |
| 5,433,321 | 7/1995 | Abidin et al. ...................... 206/354 |
| 5,528,811 | 6/1996 | Abidin et al. .................. 206/352 X |

*Primary Examiner*—Bryon P. Gehman
*Attorney, Agent, or Firm*—Beehler & Pavitt

[57] ABSTRACT

A disposable device for removing a blade from the tang of a surgical scalpel on which the blade has been removably affixed, said device comprising a rectangular plastic receptacle at least partially vertically oriented and formed of two interlocking facing halves to define an axial recess extending from the upper face of the device to terminate above the lower end of the receptacle, said recess having internal ramps and projections which disengage the blade from the tang upon insertion of the blade and tang into the recess, followed by withdrawal of the scalpel tang.

4 Claims, 2 Drawing Sheets

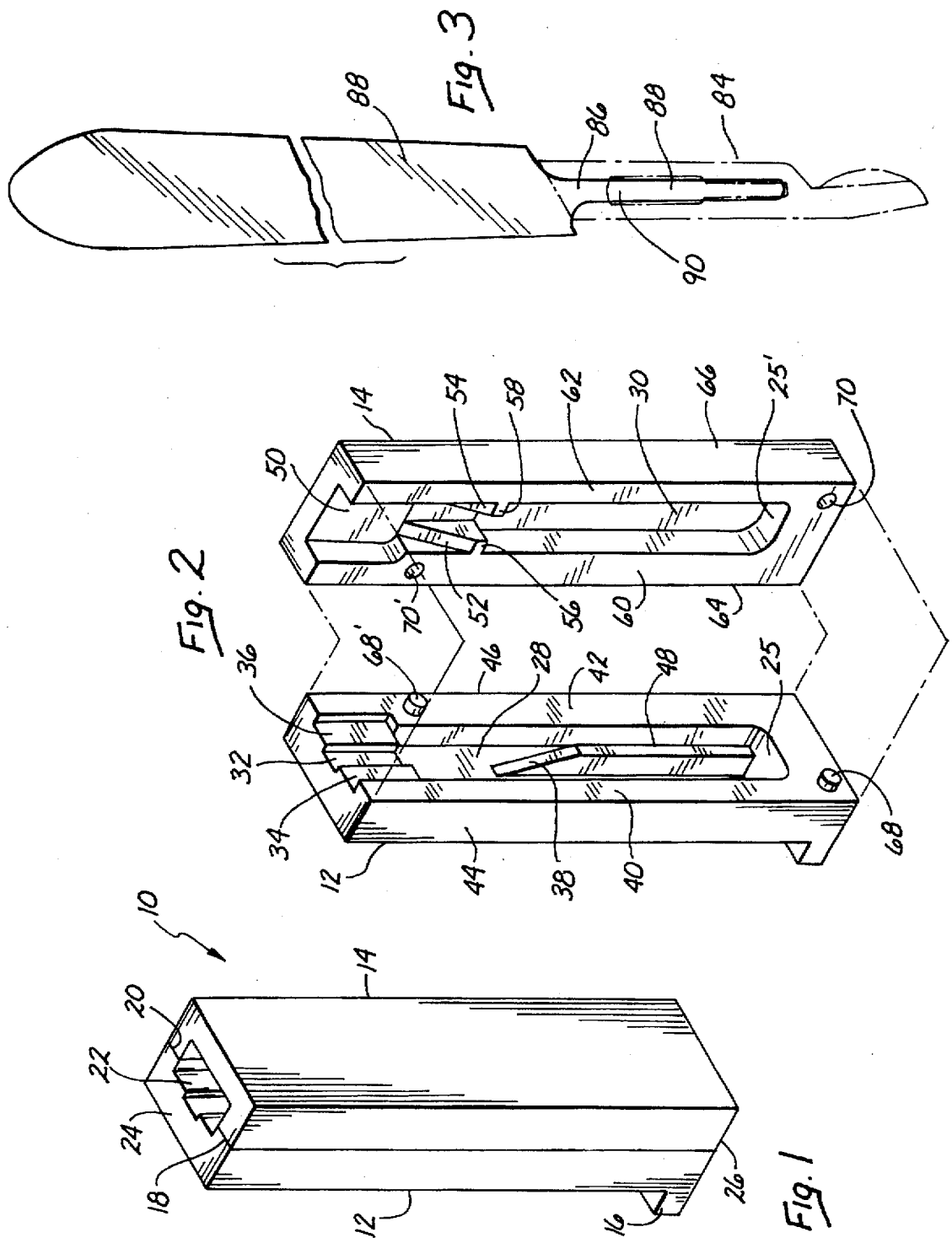

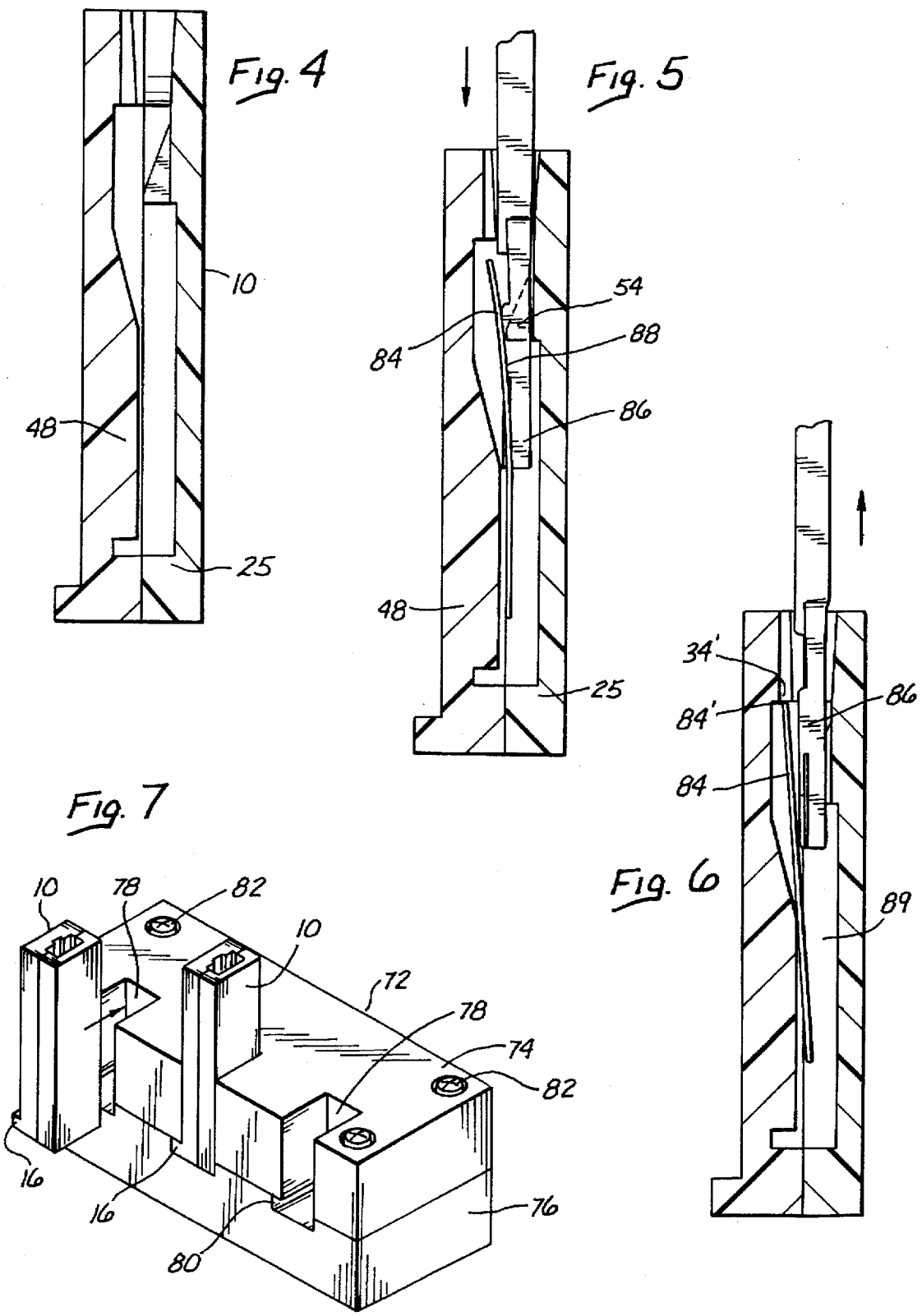

DISPOSABLE RECEPTACLE FOR REMOVING BLADES FROM A SCALPEL

FIELD OF THE INVENTION

This invention relates generally to the field of surgical instruments and more particularly to disposable devices adapted to remove a blade from a scalpel by simple insertion of the scalpel tang with its blade into the device.

BACKGROUND OF THE INVENTION

In the normal course of any surgical procedure, the surgeon may desire to have the blade on his scalpel changed numerous times since the sharpness of the blade is regarded as a prime prerequisite for effective surgery.

Initially, replaceable blades were removed manually, either by the surgeon or one of his assistants. Such manual removal of the blades has always presented the danger of a "slip" during the removal process which slip could result in cutting the flesh of the surgeon or other person undertaking the blade removal and replacement. With the advent of the danger presented by exposure to blood which may be contaminated by the HIV virus, those who may be involved in removing scalpel blades have become particularly sensitive to the possibility of being cut by a blade which may have been subjected to contact with contaminated blood. Consequently, attention has been given to devising means for effective blade removal other than manually. Thus, since at least 1981, a number of devices have been proposed to enable a surgeon to remove a blade from a scalpel without the necessity of digital contact with a possibly contaminated blade. Examples of such prior art efforts may be seen in the following United States patents: U.S. Pat. Nos. 4,168,777, 4,270,416, 4,344,532, 4,395,807, 4,466,539, 4,730,376, 4,903,390 and 5,163,553.

However, despite the teachings of these patents, the present inventor in his work as a surgeon has not found any devices made in accordance with the teachings of these patents commercially available for one reason or another. Whether this is due to complexity, expensive cost of manufacture or ineffectiveness, has not been determined. However, the need exists for an inexpensive effective disposable blade removing device, and that need has not been satisfied prior to the present invention.

SUMMARY OF THE INVENTION

The present invention comprises a heavy steel base which may be slotted to receive a plurality of removable vertically projecting disposable plastic blade removing elements. The base is preferably made of a two part steel block, one part of which is milled to receive and securely retain the upper portion of the plastic element, with the second part of the steel block being milled to receive a laterally projecting bottom flange which prevents the element from being moved out of the slots in three of the four possible directions of movement. The two block portions are secured together, preferably by threaded elements.

The disposable blade removing element is formed as a rectangular receptacle comprised of a first elongated half and a second elongated half which are brought together and secured to each other. The two halves define a single recess which extends from the top end of the rectangular receptacle down toward the bottom end. The recess in the first half of the receptacle is configured in cross section closely to conform to a portion of the lower face of the scalpel tang and the blade mounted thereon, and terminates in a wall at which the recess is expanded to form half of a rectangular channel in the center of a portion of which is provided a ramped ridge. The other half of the receptacle defines a registering recess. The recess in the second half of the receptacle is configured to provide an initial rectangular section which extends for a short distance at the end of which a pair of parallel side ramps are provided, being spaced apart from each other by the width of the scalpel tang. A short distance thereafter, the recess in the second half of the receptacle is configured to define with the other half of the receptacle, a rectangular channel into which a removed blade will be deposited.

With the recess and ramps thus described, upon inserting a blade carrying scalpel into the top of the rectangular receptacle, the trailing portion of the blade is initially pulled off the rear of the tang island by the spaced-apart ramps in the second half of the receptacle; and further insertion of the tang and blade into the recess in the receptacle results in the remaining forward portion of the blade being detached from the tang by the ramp of the central ridge in the first half of the receptacle with a tactile release and a clicking sound being heard to indicate that removal of the blade from the tang has been completed; whereupon the tang, without the blade, may be withdrawn from the top of the receptacle.

After each receptacle in the steel block retainer has received a detached blade, the receptacles may be withdrawn from the steel block retainer and disposed of, and new receptacles may be replaced in the block.

Because of the ability of the surgeon to feel the blade release and the clicking sound which occurs upon detachment of the blade from the scalpel tang, the surgeon or other person who may have inserted the bladed scalpel into the receptacle will know immediately that the blade has been detached from the scalpel tang so that the latter may be withdrawn from the opening in the receptacle. The steel block may be provided with any number of receptacles receiving recesses.

Since the receptacle is formed in two halves, these halves may be formed in multi-cavity molds and brought together and secured together by adhesive, or otherwise. Further, the receptacle halves may be formed of an inexpensive rigid polystyrene or other inexpensive plastic material. As so fabricated, they may be disposed of without regard to expense.

DESCRIPTION OF THE DRAWINGS

In the accompanying drawings,

FIG. 1 is a perspective view of the preferred embodiment of the receptacle of the present invention.

FIG. 2 is a perspective view of the receptacle of FIG. 1 in which the two halves have been exploded at right angles.

FIG. 3 is a side elevation of the scalpel showing a blade attached in phantom.

FIG. 4 is a vertical section taken through the center of FIG. 1.

FIG. 5 is similar to FIG. 4 but showing the blade end of the scalpel being inserted in the recess from the top of the receptacle.

FIG. 6 is similar to FIG. 4 but showing the scalpel tang being withdrawn from the recess after the blade has been detached from the tang.

FIG. 7 is a miniaturized perspective view of a receptacles holding block showing the manner in which receptacles are inserted and held for use in removing blades from scalpels.

DESCRIPTION OF THE PREFERRED EMBODIMENT

Referring to FIGS. 1 and 2, the receptacle 10 of the present invention is formed as an elongated rectangular block of two halves 12 and 14. The half 12 is provided with a bottom footing 16, the function of which will be hereinafter explained. The two halves 12 and 14 are brought together along their side edges 18 and 20 which preferably lie in a common vertical plane (not shown) The two halves 12 and 14 are internally molded to form a recess 22 which commences at the top face 24 of the rectangular receptacle 10 and extends downwardly to a planar bottom 25 which is spaced from the bottom face 26 of the receptacle 10. This recess 22 comprises two internal recess configurations 28 and 30 formed in the two halves 12 and 14, respectively, of the receptacle 10. The recesses 28 and 30, as may be seen from FIG. 2, are quite different in configuration.

The recess 28 commences with a rectilinear slot 32 which extends downwardly for a short predetermined distance as defined by the steps 34 and 36. At the lower ends of the slot 32 and the steps 34 and 36, the recess 28 is then deepened for the balance of the cavity down to the bottom 25. However, commencing a further predetermined distance (approximately ½ inch from the lower ends of the steps 34, 36 and the slot 32) is provided a central ramp 38 which rises to the level of the faces 40, 42 of the side walls 44, 46 of the half element 12, and continues as a ridge 48 to within a ¼ to ½ of an inch from the bottom 25 of the recess 28.

The internal configuration of the other half 14 of the receptacle 10 is quite different from that of the half 12. A passage 50 of a length approximating the length of the steps 34 and 66 is provided, at the lower portion of which arise a pair of ramps 52, 54 spaced from each other by a distance equal to the width of the slot 32 in the receptacle half 12. The rise on these ramps may extend for approximately ¼ to ⅜ of an inch, terminating in platforms 56, 58 which lie in the plane of the faces 60, 62 of the side walls 64, 66 of the element 14. The extent of the platforms 56 and 58 may be of the order of a 1/16 to ⅛ of an inch following which the recess 30 assumes the shape of a cavity corresponding to that of 28 in half 12 except for having no ramp 38 and ridge 40, and extends down to its lower end 25' which coincides with the bottom 25 of the cavity 28 in the half element 12.

The two halves 12 and 14 are brought together and adhered along their side wall faces 40, 62 to form the rectangular receptacle shown in FIG. 1. To ensure proper alignment at the times of bringing the two faces 40 and 62 together for adherence, it may be desirable to provide protruding peg-like elements 68, 68' for insertion in mating orifices 70, 70'. Such elements and orifices could be formed to enable the two halves 12 and 14 to interlock and thereby eliminates the necessity of securing the two halves together by adherence.

After a plurality of receptacles 10 have been assembled and the two halves securely adhered together by an adhesive (not shown), they are ready for insertion in a base block 72 formed of steel in two sections 74 and 76 as shown in FIG. 7. The section 74 is provided with slots 78 each being configured to slideably receive in a firm fit three sides of a receptacle 10 as shown in FIG. 7. To complete the fit, the lower portion of the steel base block 72 is cut laterally to form a slot 80 extruding parallel to 10 the slot 78, thereby to receive the footing 16 of the receptacle 10. The two halves 74, 76 of the block are brought together and secured in the overlying position shown in FIG. 7 by screws 82. Alternatively, the base block 72 could be cast or milled as a single piece.

In use, after a plurality of receptacles 10 have been securely inserted in the steel base block 72 in the manner last described, the removal of a blade 84 from the tang 86 of a scalpel 88 may readily be accomplished in the manner shown in FIGS. 5 and 6 of the drawings. Before insertion of a bladed scalpel tang, the receptacle 10 in vertical section appears as shown in FIG. 4. To effect removal of the blade 84 from the tang 86, the tang 86 is pushed into the recess 22 through the passage 50 in the receptacle half 14 and the slot 32 in the receptacle half 12, and further forced down over the ramps 52 and 54. These ramps serve to bend the blade laterally to lift it off of the tang island 88 which secures the blade to the tang 86 by the island 88 having been passed through a slot 90 in the blade 84. As the blade 84 is thus detached from the tang island 88, there is produced a clicking sound, thereby indicating that the blade has been detached from the tang, and the surgeon can feel that such detachment has occurred. Upon reversing the direction of the tang 86 in the recess 22 to withdraw it, the upper end 84' of the blade 84 will strike the inner ends 34' and 36' (not shown) of the steps 34, 36, respectively, thereby retaining the blade 84 will then drop back into the cavity 89 comprised of the two half cavities 28 and 30.

With withdrawal of the tang 86, the latter may then be provided with a replacement blade and the discarded blade 84 left in the receptacle 10 where it has been deposited. At any convenient point in the course of the surgery or thereafter, the receptacle 10 carrying the discarded blade 84 may be slid out of the slots 78, 80 and the steel block 72 and discarded. Thereby, it is unnecessary for the surgeon or any assistant to touch the blade to accomplish its removal from the scalpel tang 86. The latter may then be scrubbed with disinfectant or autoclaved before a replacement blade is affixed to the tang 86 which, at the present time, is accomplished manually. Also, after all receptacles 10 have been removed from the steel base block 72, the latter may also be autoclaved or otherwise sterilized.

A particular advantage of the receptacle and its mounting blade of the present invention is the fact that when detachment of the blade has been effected, upon insertion of the bladed tang into the receptacle recess, a clicking sound is produced, thereby to indicate that the scalpel tang may be withdrawn from the receptacle.

I claim:

1. A device for removing a blade from the tang of a surgical scalpel, the scalpel including an elongated gripping section having a butt end and an oppositely extending tang end, the tang end being flattened with a first upper face and a second opposite lower face, the faces being joined in parallel register along their sides by edges normal to the faces, the first upper face having an elongated upwardly protruding boss coincident with the upper face and extending for a first predetermined distance, the boss having a forward end and an after end, and side edges, the side edges of the boss having slotting commencing at the forward end of the boss, the slotting initially being parallel to the upper face of the tang and angling rearwardly and upwardly to terminate at the after end of the boss; and a blade, the blade being configured for mounting on the first upper face of the tang to extend further axially beyond the tang and laterally from the side edges of the tang, the blade having an elongated opening comprising a forward section of a width to accommodate the slotted forward end of the boss and a wider after section to accommodate the after section of the boss, whereby the after section in the opening in the blade may be placed over the boss on the tang and the blade mounted on the tang by sliding the blade rearwardly to cause the slotting in the side edges of the boss to receive the forward section of the blade opening and to seat the blade in the upwardly extending slotting terminating at the after end of the boss, said device comprising:

a rectangular receptacle at least partially vertically oriented, said receptacle being comprised of a first elongated half and a second elongated half secured to each other in register to form a unitary block with a rectangular forward end, each of said halves being recessed axially inwardly from said forward rectangular end, the recess in the first half being configured for a second predetermined distance in a cross section closely conforming of the lower face of the tang and the blade mounted on the tang, and terminating in a wall beyond which wall a portion of the recess, as it extend further axially, is expanded to a rectangular configuration to receive a blade after detachment from the tang, said expanded portion of the recess having a centrally disposed ramp rising from a point a third predetermined distance from the wall and extending toward the bottom of the recess;

the recess in the second half of the receptacle being configured to provide an initial rectangular passage for said second predetermined distance at the end of which passage is provided a pair of parallel side ramps spaced apart from each other by the width of the tang, said ramps rising for the third predetermined distance from the end of the initial rectangular passage to the level of the upper edge of the second half of the receptacle, each of said ramps terminating in a vertical wall which wall a portion of the recess is fully expanded to the approximate cross section of its initial rectangular passage; said first and second receptacle halves, when secured to each other with their recesses in register, serving to remove the blade from the tang of the scalpel when the blade is inserted into the receptacle through the registering initial portions of the recesses of its first and second halves, and the blade mounted on the tang has been pushed as far as possible into the recesses, and the tang is withdrawn when the receptacle is held firmly in a position against axial or lateral movement, whereupon the blade is detached from the tang, so that upon withdrawing the scalpel tang from the receptacle, the blade is left deposited in the recesses in the two registering halves of the receptacle; and means to removably secure the receptacle in an at least partially vertical orientation.

2. The device as described in claim 1, wherein the means to removably secure the receptacle is a metal block, each said block having at least one slot extending inwardly from a side of the block, each said slot being at least partially vertically oriented and configured and dimensioned to receive the lower end of the receptacle in a fit which prevents movement of the receptacle in all directions except the direction toward the side of the block from which the slot extends.

3. The device as described in claim 2 wherein the base of each slot is recessed laterally, and the bottom end of the receptacle is provided with a laterally projecting flange adapted to extend into and along each lateral recess in the base of the slot.

4. The device as described in claim 3 wherein the metal block is comprised of first and second steel sections, the first section being placed one on top of the second section, the first section being milled to provide at least one receptacle and slot, and the second section defining the bottom of each slot and receptacle, and both sections being secured together by fastening means.

* * * * *